United States Patent
Robertsson et al.

(10) Patent No.: US 10,893,981 B2
(45) Date of Patent: Jan. 19, 2021

(54) WOUND DRESSING WITH A BACTERIAL ADSORBING COMPOSITION AND MOISTURE HOLDING SYSTEM

(71) Applicant: Abigo Medical AB, Askim (SE)

(72) Inventors: Peter Robertsson, Lomma (SE); Jan G. Smith, Askim (SE)

(73) Assignee: Abigo Medical AB, Gothenburg (SE)

( * ) Notice: Subject to any disclaimer, the term of this patent is extended or adjusted under 35 U.S.C. 154(b) by 408 days.

(21) Appl. No.: 15/256,841

(22) Filed: Sep. 6, 2016

(65) Prior Publication Data
US 2016/0367405 A1 Dec. 22, 2016

Related U.S. Application Data

(62) Division of application No. 11/654,854, filed on Jan. 18, 2007, now Pat. No. 9,463,119.

(51) Int. Cl.
*A61F 13/00* (2006.01)
*A61F 13/06* (2006.01)
(Continued)

(52) U.S. Cl.
CPC .. *A61F 13/00029* (2013.01); *A61F 13/00021* (2013.01); *A61F 13/069* (2013.01);
(Continued)

(58) Field of Classification Search
CPC .......... A61F 13/00029; A61F 13/00021; A61F 13/069; A61F 2013/00217; A61F 2013/00319; A61F 2013/0054; A61F 2013/00634; A61F 2013/00638; A61F 2013/0074; A61F 2013/00744;
(Continued)

(56) References Cited

U.S. PATENT DOCUMENTS 4,211,227 A 7/1980 Anderson et al.
4,617,326 A 10/1986 Björnberg et al.
(Continued)

FOREIGN PATENT DOCUMENTS

EP 0021230 1/1981
EP 0666081 8/1995
(Continued)

OTHER PUBLICATIONS

Arnall, David "The Family of Wound Care Products" http://jan.ucc.nau.edu/~daa/woundproducts/products.html, 23 pages (last updated Sep. 9, 1999).
(Continued)

*Primary Examiner* — Ophelia A Hawthorne
(74) *Attorney, Agent, or Firm* — Myers Bigel, P.A.

(57) ABSTRACT

The invention herein relates to a wound dressing product, combining a hydrophobic fabric, which is to be placed towards the wound, and is capable of binding unwanted microorganisms, and a moisture carrying matrix such as a gel or a foam. The product of the invention is ideal for treatment of drier wounds. It protects the wound and reduces the number of pathogenic microorganisms, without using antimicrobial substances and at the same time adds or traps moisture to the wound both supporting the hydrophobic functioning of the pad and healing in general by keeping the wound moist.

25 Claims, 2 Drawing Sheets

(51) Int. Cl.
*A61L 15/42* (2006.01)
*A61L 15/60* (2006.01)

(52) U.S. Cl.
CPC ............. *A61L 15/425* (2013.01); *A61L 15/60* (2013.01); *A61F 2013/0054* (2013.01); *A61F 2013/0074* (2013.01); *A61F 2013/00217* (2013.01); *A61F 2013/00319* (2013.01); *A61F 2013/00634* (2013.01); *A61F 2013/00638* (2013.01); *A61F 2013/00744* (2013.01); *A61F 2013/00748* (2013.01)

(58) Field of Classification Search
CPC .......... A61F 2013/00748; A61F 13/023; A61F 13/0266; A61F 2013/00089; A61L 15/425; A61L 15/60
See application file for complete search history.

(56) References Cited

U.S. PATENT DOCUMENTS

| | | | |
|---|---|---|---|
| 4,655,756 | A | 4/1987 | Fawkes |
| 4,678,704 | A | 7/1987 | Fellows |
| 4,921,704 | A * | 5/1990 | Fabo ................. A61F 13/00021 424/446 |
| 5,098,417 | A | 3/1992 | Yamazaki et al. |
| 5,147,338 | A * | 9/1992 | Lang ................. A61F 13/00046 602/47 |
| 5,231,992 | A | 8/1993 | Leon |
| 5,271,043 | A | 12/1993 | Bogart et al. |
| 5,340,363 | A | 8/1994 | Fabo |
| 5,670,169 | A | 9/1997 | Cornell et al. |
| 5,700,742 | A | 12/1997 | Payne |
| 5,707,736 | A | 1/1998 | Levy et al. |
| 5,817,325 | A | 10/1998 | Sawan et al. |
| 5,856,248 | A | 1/1999 | Weinberg |
| 5,939,339 | A * | 8/1999 | Delmore ............. A61F 13/0273 428/354 |
| 5,941,840 | A | 8/1999 | Court et al. |
| 6,160,196 | A | 12/2000 | Knieler et al. |
| 6,369,289 | B1 | 4/2002 | Orr, III |
| 2004/0030304 | A1* | 2/2004 | Hunt ................. A61F 13/00042 604/317 |
| 2004/0082925 | A1 | 4/2004 | Patel |
| 2006/0129080 | A1* | 6/2006 | Bjornberg ......... A61F 13/00042 602/41 |
| 2006/0163149 | A1 | 7/2006 | Wadstrom et al. |
| 2006/0165761 | A1 | 7/2006 | Trotter |
| 2006/0219080 | A1* | 10/2006 | Heid ........................ G01N 1/06 83/651 |
| 2006/0241542 | A1* | 10/2006 | Gudnason ........... A61F 13/0203 602/59 |
| 2008/0249485 | A1 | 10/2008 | Effing |
| 2008/0254015 | A1 | 10/2008 | Taktak et al. |

FOREIGN PATENT DOCUMENTS

| | | |
|---|---|---|
| EP | 0945144 | 9/1999 |
| WO | 9407935 | 4/1994 |
| WO | 0209782 | 2/2002 |
| WO | WO 2005/067991 A2 | 7/2005 |
| WO | 2007002705 | 1/2007 |

OTHER PUBLICATIONS

Eisenbud, David et al. "Hyrdogel Wound Dressings: Where Do We Stand in 2003?" Ostomy Wound Management, 49(10), 9 pages (2003).

European approval for Acticoat moisture control product, European approval Apr. 1, 2006—FDA approval Apr. 2005, 2 pages.

FDA "510(k) Summary for SoloSite Gel Conformable Dressing" Letter of Marketing Allowance, 7 pages (1998).

FDA "510(k) Notification Summary for Sorbact® Wound Dressings" Letter of Marketing Allowance, 8 pages (2007).

Hallern, B. V. et al. "Cutisorb Sorbact—Nonpharmacologic antibacterial therapy in traumatology and surgery" Praxis aktuell, Postoperative Wound Dehiscence, 8 pages (2004).

Hallern, B.V. et al. "Has Cutisorb Sorbact proved its practical value as an antibacterial dressing?" Medizin & Praxis Spezial, Infected Wounds, 7 pages (2005).

Hallern, B. V. et al. "Removal of wound bacteria from infected and colonized wounds with Cutisorb Sorbact" Medizin & Praxis Spezial, Disturbances of Wound Healing, 11 pages (2004).

Hess, Cathy Thomas "Clinical Guide: Wound Care" Third Edition, Springhouse Corporation, pp. 177-314 (2000).

Thomas, Stephen, "Allevyn" Handbook of Wound Dressings, 1994 Edition, Journal of Wound Care, 2 pages (1994).

Thomas, Stephen, "Tielle" Handbook of Wound Dressings, 1994 Edition, Journal of Wound Care, 2 pages (1994).

Thomas, Stephen, "Vigilon" Handbook of Wound Dressings, 1994 Edition, Journal of Wound Care, 3 pages (1994).

Vasel-Biergans, Anette "IntraSite Conformable" Wundauflagen für die Kitteltasche, Wissenschaftliche, pp. 139-140 (2006).

Vasel-Biergans, Anette "Mepilex products with Safetac Technology" Wundauflagen für die Kitteltasche, Wissenschaftliche, pp. 282-287 (2006).

Voggenreiter, Dold "Wundtherapie" Thieme, pp. 36-39 (2004).

Wilson, F. et al. "Verbandmittel Krankenpflegeartikel Medizinprodukte" 8th Edition, 25 pages (2003).

Notice of Opposition corresponding to European Patent No. EP 2 114 470 (42 pages) (dated Dec. 7, 2018).

* cited by examiner

Fig 2C

WOUND DRESSING WITH A BACTERIAL ADSORBING COMPOSITION AND MOISTURE HOLDING SYSTEM

BACKGROUND OF THE INVENTION

Field of the Invention

The invention herein relates to a wound dressing product, combining a hydrophobic fabric, facing towards the wound and being capable of binding unwanted micro organisms, together with a moisture holding material such as a gel or a foam or the like. The product is ideal for the treatment of drier wounds Description of the Related Art The problem in healing of wounds associated with high bacterial loads is, for example, tissue damage by release of toxins and enzymes and possible spread of infections to the blood stream. Studies have also shown that high tissue counts of microorganisms as well as dry wounds delay wound healing.

Numerous studies during the last few decades have also shown that bacteria, such as *Staphylococcus aureus* and Group A streptococci, both common wound pathogens, and the yeast *Candida albicans*, commonly express profound cell surface hydrophobicity.

Several structures which render the cell surface hydrophobic have been defined, such as the fimbriae of *E. coli* which mediate adhesion to the intestinal wall, proteins on *C. albicans* which has been called "hydrophobins", and lipoteichoic acid in the cell wall of Gram-positive bacteria.

According to the hydrophobic principle of the laws of nature, a system will always struggle towards lowest possible energy consumption. When two water repellent molecules come into collision with each other they will increase the entropy and create disorder. The water molecules that surround the two hydrophobic molecules will force them together by hydrogen bonds between the water molecules although there is no force of attraction between the hydrophobic interactions, and will expel water molecules.

The initial step of infections of the skin and mucosal surfaces is microbial adhesion to wounded tissues. Several microbial components that adhesively bind to specific receptors have been identified, such as fimbriae of Gram-negative enteric bacteria. Initial adhesion can be mediated by hydrophobic interactions between microbes and host tissue structures, and also by charge interactions. Binding of extra cellular matrix and serum proteins, like fibronectin, collagen and fibrinogen may further enhance colonization of deeper wound tissue.

In wound treatment, after tissue colonization, wound microbes multiply causing tissue damage by release of toxins and enzymes, and may even spread to the blood stream. The human body has multiple defence mechanisms, for example the innate defence system. Also specific antibodies directed against the colonizing microorganism may be active to decrease the number of microorganisms. Numerous studies have shown that high tissue counts of microorganisms delay wound healing. On the other hand, small numbers of bacteria were shown to enhance the wound healing process in rodents by stimulating production of collagen-hydroxyproline.

Conventional treatment of wounds consists of mechanical cleansing with water, buffer solutions or disinfectants to remove bacteria and debris. This is of importance since debris hampers wound healing. The use of oxidizing agents (for example iodine tincture) or antiseptics (for example ointments comprising silver sulphadiazine) have been known for a long time. A number of disadvantages to these methods can be mentioned. For example, bacteria which have died remain in the wound, and wounds cannot be cleaned to remove the active compound reliably after the application, since it spreads in the entire wound. If these active compounds occur freely in the wound, they can also attack cells and substances in the wound fluid which promote wound healing.

Another method of wound treatment is the use of local antibiotics. Microbiologists disapprove of the use of local antibiotics since this is known to induce antibiotic resistance. Also, in order to protect an already cleaned wound, including wounds from surgical cuts, various kinds of Band-Aid's, surgical tapes and dressings and the like have been used. Various kinds of cleaning and anti-microbial compounds added to such products been added or suggested for more long time effects.

A more modern and overall effective method (the so called Sorbact-principle) is the use of a product combining both a traditional dressing with a mounted absorbent material plus a hydrophobic fabric which is capable of binding unwanted microorganisms and is attached to the absorbent material and placed towards the wound, this is described in U.S. Pat. No. 4,617,326 and patent application WO2006/062470A1. Products containing pads of bacteria-binding fabric and absorbing fabric, to be held together and on a wound by a bandage or tape, already exist in the market. However the problem with such solutions being based on the hydrophobicity of unwanted microorganisms in the wound and their binding ability to the integrated hydrophobic fabric of the dressing, is that they require a certain amount of moisture for the hydrophobic binding to occur. This is not a problem in most cases as wound fluids are available, but in some special cases, for example foot-wounds of diabetics or other dry wounds there is a need for additional moisture.

A diabetic foot ulcer is an open sore or wound that most commonly occurs on the bottom of the foot in approximately 15 percent of patients with diabetes. Of those who develop a foot ulcer, six percent will be hospitalized due to infection or other ulcer-related complication.

Diabetes is the leading cause of nontraumatic lower extremity amputations in the United States, and approximately 14 to 24 percent of patients with diabetes who develop a foot ulcer have an amputation. Anyone who has diabetes can develop a foot ulcer. Native Americans, African Americans, Hispanics and older men are more likely to develop ulcers. People who use insulin are at a higher risk of developing a foot ulcer, as are patients with diabetes-related kidney, eye, and heart disease. Being overweight and using alcohol and tobacco also play a role in the development of foot ulcers.

Ulcers form due to a combination of factors, such as lack of feeling in the foot, poor circulation, foot deformities, irritation (such as friction or pressure), and trauma, as well as duration of diabetes. Patients who have diabetes for many years can develop neuropathy, a reduced or complete lack of feeling in the feet due to nerve damage caused by elevated blood glucose levels over time. The nerve damage often can occur without pain and one may not even be aware of the problem. Your podiatric physician can test feet for neuropathy with a simple and painless tool called a monofilament.

Vascular disease can complicate a foot ulcer, reducing the body's ability to heal and increasing the risk for an infection. Elevations in blood glucose can reduce the body's ability to fight off a potential infection and also retard healing.

Foot ulcers in patients with diabetes should be treated for several reasons such as, reducing the risk of infection and amputation, improving function and quality of life, and reducing health care costs. The primary goal in the treatment of foot ulcers is to obtain healing as soon as possible. The faster the healing, and reduced number of unwanted microorganisms in the wound, the less chance for a problematic infection. For optimum healing, ulcers, especially those on the bottom of the foot, must be "off-loaded." Patients may be asked to wear special footgear, or a brace, specialized castings, or use a wheelchair or crutches. These devices will reduce the pressure and irritation to the ulcer area and help to speed the healing process.

The science of wound care has advanced significantly over the past ten years. The old thought of "let the air get at it" is now known to be harmful to healing. We know that wounds and ulcers heal faster, with a lower risk of infection, if they are kept covered and moist. The use of full strength betadine, peroxide, whirlpools and soaking are not recommended, as this could lead to further complications.

There are several known inventions relating to the use of antimicrobial substances and materials. One such example is the U.S. Pat. No. 6,369,289, which discloses the use of a cellulosic bandage in a method for covering an open wound by contacting the wound with the bandage having a calculated amount of antimicrobial agent. The disclosure of this patent and all other patents referred to herein is incorporate herein by reference. U.S. Pat. No. 4,655,756, relates to a non-woven material treated with a linear polymeric biguanide having a defined formula, or a mixture of, e.g., polyhexamethylene biguanide (PHMB).

Other types of antimicrobial agents are also known. For example, U.S. Pat. No. 5,707,736 discloses a dry, disposable, polymeric product having sustained-release antimicrobial activity that is formed from a polymeric material having an amine salt antimicrobial agent incorporated therein. The polymeric material may be in the form of fibbers, sheets, films, and other stable woven, nonwoven and knitted materials. The antimicrobial agents include, e.g., chlorhexidine gluconate and chlorhexidine hydrochloride. Several similar uses of dressings combining antimicrobial compounds are known.

U.S. Pat. No. 4,678,704 describes an impregnated fabric material comprising a fabric substrate to which has been applied an active cationic impregnate along with an anionic indicator dye in combination with a further cationic component, wherein the dye bonds to the further cationic component more readily than to the substrate and the further cationic component competes with the impregnated for bonding to the dye. The cationic imp regnant may be a polymeric biguanide.

U.S. Pat. No. 5,098,417 relates to a wound dressing for systemic administration of a physiologically- or biologically-active agent by controlled release of the agent into such wound. The wound dressing comprises a substrate in the form of a fabric or cloth, at least a portion of which is cellulosic, which has been chemically modified to convert hydroxyl groups in the cellulosic portion to ionic-adsorbing sites, an ionic form of a physiologically- or biologically-active agent (which includes antibacterial agents) adsorbed in the substrate. The ionic bonds hold the agent temporarily to the substrate for controlled release therefrom in proportion to the amount of exudate in contact with the substrate and are formed by adsorbing the agent on the substrate at room temperature. The ionic bonds are disassociated upon contact with body exudate from wounds thereby to release the physiologically- or biologically-active agent in an amount in proportion to the amount of exudate in contact with the substrate.

U.S. Pat. No. 5,700,742 relates to a method of treating a textile material to inhibit microbial growth, which comprises applying to the textile material an oligo or polymeric biguanide or salt thereof with an inorganic acid or an organic acid having a pK value above 4.5 followed by a strong organic acid having a pK value below 4.5 and free from any aliphatic or oxyalkylene chain containing 12 or more carbon atoms. A textile material treated in accordance with the claimed method is also disclosed.

U.S. Pat. No. 5,856,248 relates to cellulose fibers and products comprising cellulose fibres treated to absorb body secretions while substantially decreasing microbial growth, the fibres being chemically modified in a two-stage process comprising a first stage treatment with a water soluble salt of a transition metal and an alkali and a second stage treatment with a solution of a bisbiguanide compound, thereby forming a bond between the cellulose fibres, the transition metal and the compound. The process may utilize a rinsing step to neutral pH between the two aforementioned stages.

U.S. Pat. No. 5,817,325 relates to an article of manufacture having disposed on a surface thereof a contact-killing, non-leaching antimicrobial coating that kills microorganisms upon contact. The coating comprises an organic polycationic polymer matrix immobilized on the surface having bound or complexed thereto a surface-accessible antimicrobial metallic material such that the antimicrobial material does not release biocidal amounts of elutables into the surrounding environment.

Other patents relate to the so-called SORBACT® products, which are folded dressing compositions including a hydrophobic fabric and a hydrophilic, liquid-absorbing material. U.S. Pat. No. 4,617,326 describes this principle. Further, U.S. Pat. No. 6,160,196 relates to the same principle but adds thereto an antimicrobial active compound which is adapted to prevent infections from the outside of the pad, the antimicrobial compound is not be released into the wound. U.S. Pat. No. 4,211,227 discloses a non-woven surgical sponge material comprising a layered fabric having an inner core or a substantially hydrophilic material disposed adjacent at least one outer or surface layer, or between a pair of outer layers, of a substantially hydrophobic material. The sponge material is bonded by passing the material through rolls engraved in a pattern of lands and grooves such that a repeating pattern of three degrees of compression are imposed on the material. However, the so produced sponge is using polyester fibres as the hydrophobic material, consequently the hydrophobic properties to bind microbes is not as effective as in the invention herein. Nor does the invention have the moisturizing properties as in the invention herein.

Since all microbes as well as viruses are negatively charged U.S. Patent application 2006/0163149 relates to an electrostatic method for absorption purposes. This application discloses an in water insoluble support matrix wherein the support matrix is substituted with a hydrophobic entity which in turn is connected to a positively charged entity. The invention also relates to a product for absorption purposes comprising a first support matrix connected to a hydrophobic entity and a second support matrix connected to a positively charged entity. Further the invention also relates to a product for absorption purposes comprising a support matrix wherein the support matrix is substituted with a hydrophobic entity and a positively charged entity. However the inventors do not discloses the moisturizing effect of the present invention.

U.S. Patent application 20040082925 describes a medical dressing containing an antimicrobial agent. The medical dressing comprises a layered fabric comprising an inner layer of substantially hydrophilic material, an outer layer of substantially hydrophobic material on both sides of the inner layer. Unlike the invention herein the applicants use an antimicrobial agent. Also they do not mention the moisturizing effect of the present invention.

Utilizing the so-called SORBACT® principle discussed above, products such as the SORBACT® pad consist of acetate gauze and cotton gauze treated with the fatty acid ester, for example DACC (dialkyl carbamoyl chloride) or an AKD (alkyl ketene dimer). This provides Sorbact pads with a strong hydrophobic property. When the Sorbact pad comes in contact with pathogenic microorganisms in the wound surface, the microorganisms adhere to the pad through hydrophobic interaction. The method is based on the principle that two hydrophobic surfaces bind to each other, when getting in physical contact. The SORBACT® pad consists of two components. The first component has one or more liquid permeable layers of a hydrophobic, bacteria adsorbing, physiologically innocuous material containing a woven or nonwoven hydrophilic fabric. The fabric has been rendered hydrophobic by chemical treatment with a compound containing hydrophobic groups. The second component consists of one or more layers of a hydrophilic, liquid adsorbing, physiologically innocuous material. The hydrophilic liquid absorbing material effects a liquid flow by suction of exudate from the wound. If the microorganisms exhibit hydrophobic surface structures they will accompany this flow of liquid and come in contact with the hydrophobic component and bind.

Even if the traditional SORBACT® pad product solves an important problem of reducing the number of microorganisms in a wound without using chemicals or antibiotics, however the problem with such solutions being based on the hydrophobicity and/or electrostatic solutions, (such as described in U.S. Patent application 2006/0163149) of unwanted microorganisms in the wound and their binding ability to the integrated hydrophobic and/or electrostatic fabric of the dressing, is that they require a certain amount of moisture for the hydrophobic binding to occur. This is not a problem in most cases as wound fluids are available, but in some special cases, for example foot-wounds of diabetics or other dry wounds there is a need for additional moisture.

Now, therefore the invention herein was made to address the above problems. It is an object of the invention herein to provide an integrated product ideal for the treatment of wounds, especially drier wounds, and a method of making this product. It is a further object of the invention to in an integrated fashion provide a product that protects the wound, absorbs exudate and reduces the number of pathogenic microorganisms, without using antimicrobial substances and adding moisture to the wound both supporting the hydrophobic functioning of the dressing and healing in general by keeping the wound moist.

SUMMARY OF THE INVENTION

The invention herein relates to a wound pad product, with a hydrophobic and/or electrostatic fabric, which is to be placed towards the wound, and is capable of binding unwanted microorganisms, integrated with a moisture-holding matrix such as a gel or foam. The product of the invention is ideal for treatment of drier wounds. It protects the wound and reduces the number of pathogenic microorganisms, without using antimicrobial substances and at the same time adds or traps moisture to the wound both supporting the hydrophobic functioning of the pad and healing in general by keeping the wound moist. The invention consists basically of two layers: a moisture carrying matrix, such as a gel or a moisture trapping matrix such as a foam and a hydrophobic cellulose acetate fabric which binds microorganisms.

Other objects and features of the inventions will be more fully apparent from the following disclosure and appended claims.

BRIEF DESCRIPTION OF THE DRAWINGS

FIGS. 1a-1c show the gel-based product. The figures are schematic drawings of a cross-sectional side view of the invention as it may be used. In FIG. 1a, the product is shown above a wound surface, on which there are bacteria schematically shown, before placement of the product on the wound. In FIG. 1b, the product is shown on the wound surface. In FIG. 1c, the product is shown upon removal from the wound.

FIGS. 2a-2c show the foam-based product. The figures are schematic drawings of a cross-sectional side view of the invention as it may be used. In FIG. 2a, the product is shown above a wound surface, on which there are bacteria schematically shown, before placement of the product on the wound. In FIG. 2b, the product is shown on the wound surface. In FIG. 2c, the product is shown upon removal from the wound.

DETAILED DESCRIPTION OF THE INVENTION AND

Preferred Embodiments Thereof

The product of the invention is ideal for treatment of drier wounds. It protects the wound, absorbs exudate and reduces the number of pathogenic microorganisms, without using antimicrobial substances and adds moisture to the wound both supporting the hydrophobic functioning of the pad and healing in general by keeping the wound moist. The product of the invention consists basically of two layers: a moisture carrying matrix, such as a gel or a moisture trapping matrix such as a foam and a hydrophobic cellulose acetate fabric which binds microorganisms.

The SORBACT® method is based on the effect that pathogenic microorganisms displays a cell surface hydrophobicity. By using a fabric or similar structure treated to become hydrophobic, this surface will then bind to the unwanted microorganisms, making it possible to remove them from a wound when the pad with the treated fabric is removed. This removal of unwanted microorganisms will be made without any development of resistance or other side-effects such as allergies or cytotoxicity, Also wounds with low secretion of wound fluids and dry wounds have many times a too high level of unwanted microorganisms for proper wound healing and there is also a concern for various infections. To be able to use the safe and effective means of the SORBACT® method to remove microorganisms from surfaces such as wounds also in drier conditions, we have in the invention herein incorporated a SORBACT® pad with specifically developed hydrogels or foams or the like. The gel contains water which is donated to the wound surface when the product of the invention is applied. The foam contains no water or to only a small extent, but the foam helps trapping the small amounts of moisture secreted from the skin, helping the hydrophobic interaction between the SORBACT® pad and the wound surface. The gel or the foam, when adding or trapping moisture to the surface also helps in the healing of the wound and further reduces the risk of the pad sticking to the wound surface and thereby aid in it's removal.

The Gel Based Product

Figure 1A:
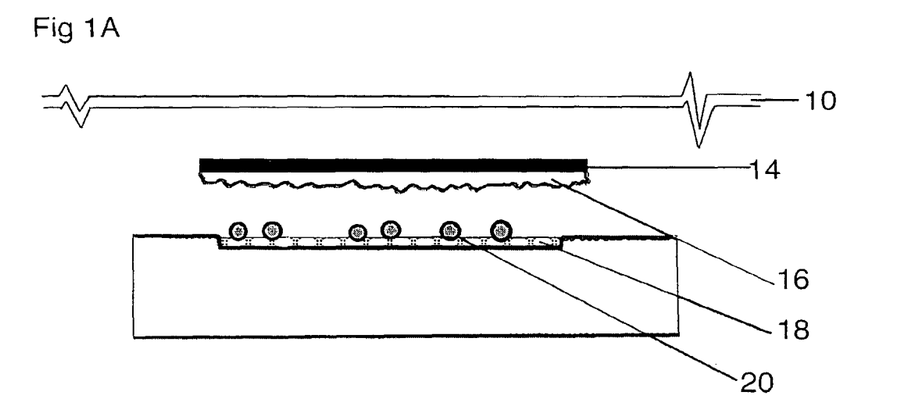
Figure 1B:
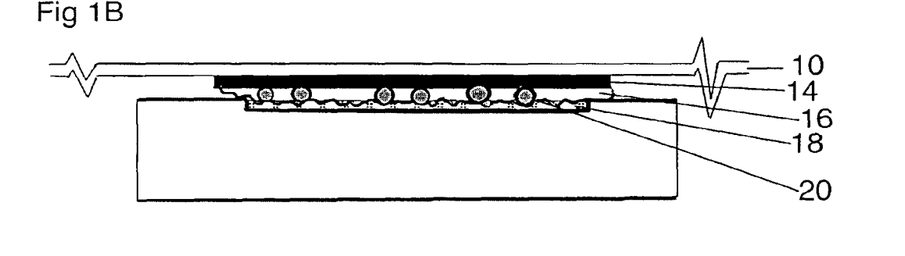
Figure 1C:
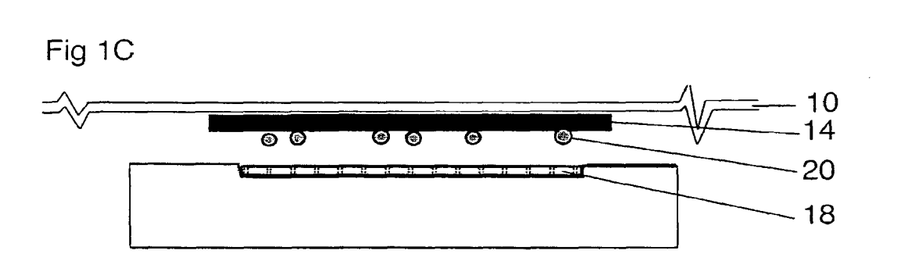

Referring to the figures, FIGS. 1a-1c are a schematic representation of the use of the invention to bind microorganisms, showing the holding material 10, hydrophobic layer 14, and a gel layer 16, above a wound area 18, on which bacteria 20, are depicted, showing sequentially before, during and after application to a wound, respectively.

The hydrophobic layer 14 is coated with a moisture-carrying layer of gel 16. Since the gel layer 16 is fluid it gets integrated with the hydrophobic layer 14. The product is held in place over the wound by the holding material 10, being cotton gauze, various band-aid, wound dressings or the like.

The hydrophobic material may comprise, for example, a hydrophobic fabric or hydrophobic non-woven fabric, or a hydrophilic fabric or non-woven fabric which has been rendered hydrophobic by a special treatment, or a hydrophobic, perforated foil. Hydrophobic woven and non-woven fabrics may be produced from synthetic fibers or the type polyamide, polypropylene and polytetrafluoroethylene fibers, or from carbon fibers. In order to obtain a hydrophobic material from a woven or non-woven hydrophilic fabric, such as woven or non-woven cotton fabric, the fabric may be treated chemically for example, in a known manner, with a compound containing hydrophobic groups, for example with a DACC such as dihexadecyl-carbamoyl chloride or dioctadecyl-carbamoyl chloride or an AKD.

A preferred hydrophobic layer of the invention is made of green cellulose acetate to which dioctadecyl carbamoyl chloride is applied as discussed in the examples.

The gel can be based on for example Carboxymethyl cellulose, Polysaccharides, Polymers, NaCl and Glycerin.

The Foam Based Product

Figure 2A:
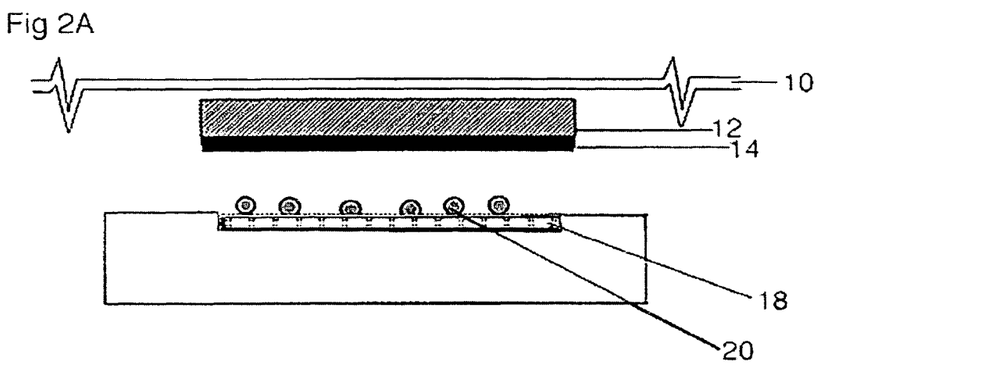
Figure 2B:
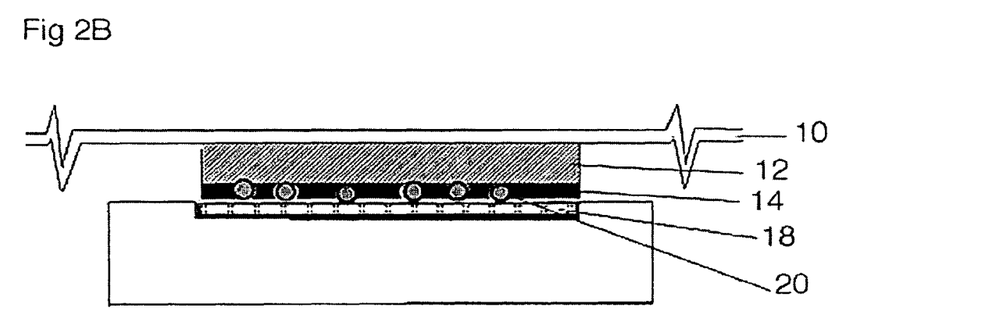
Figure 2C:
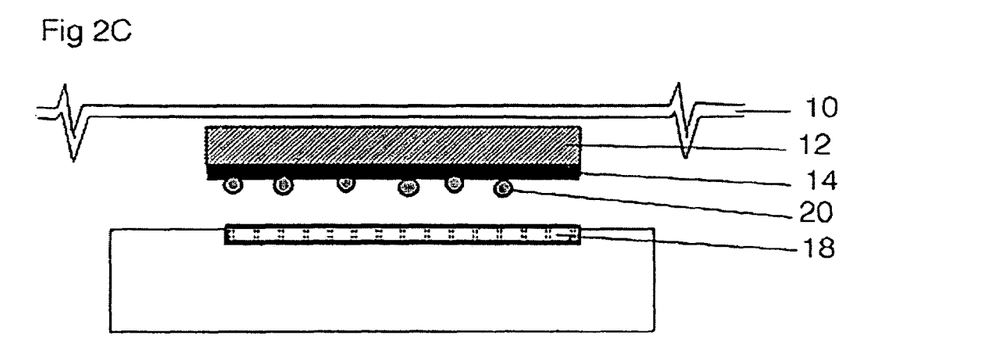

FIGS. 2a-2c are a schematic representation of the use of the invention to bind microorganisms, showing the holding material 10, foam layer 12, and a hydrophobic layer 14, above a wound area 18, on which bacteria 20, are depicted, showing sequentially before, during and after application to a wound, respectively.

In the foam product, the hydrophobic layer 14 is placed between the foam layer 12 and the wound site 18. The product is hold in place over the wound by the holding material 10, being cotton gauze, various band-aid, wound dressings or the like. The hydrophobic material may comprise, for example, a hydrophobic fabric or hydrophobic non-woven fabric, or a hydrophilic fabric or non-woven fabric which has been rendered hydrophobic by a special treatment, or a hydrophobic, perforated foil. Hydrophobic woven and non-woven fabrics may be produced from synthetic fibers or the type polyamide, polypropylene and polytetrafluoroethylene fibers, or from carbon fibers. In order to obtain a hydrophobic material from a woven or non-woven hydrophilic fabric, such as woven or non-woven cotton fabric, the fabric may be treated chemically for example, in a known manner, with a compound containing hydrophobic groups, for example with a DACC such as dihexadecyl-carbamoyl chloride or dioctadecyl-carbamoyl chloride or an AKD.

A preferred hydrophobic layer of the invention is made of green cellulose acetate to which dioctadecyl carbamoyl chloride is applied as discussed in the examples.

The hydrophobic material is bonded to foam layer with the aid of a suitable adhesive, for example Disponal 70 (Limgrossisten AB, Norrkoping, Sweden). Other adhesives known in the art could also be used.

The bonded hydrophobic layer of the Cellulose Acetate is attached to a moisture-trapping layer of foam. The foam can be based on for example Polyether, Polyester and Cellulose.

The microorganisms will be removed from the wound when the dressing is changed. Hence, the number of microorganisms decreases over time to a number which the body can control and the wound can heal. Since microbes adhere to the dressing by hydrophobic interactions, spread of microorganisms to the environment during changing of dressings is limited. The combined bacteria-binding capacity and absorption of wound secretion, pus and debris provide optimal cleansing of the wound. With this method, the bacterial load in the wound surface is reduced rapidly and effectively. The body's own defense mechanism can then take over, and the natural healing process can continue. The use of a hydrophobic layer, even without systemic antibiotic therapy, decreases the number of infecting microorganisms but does not eliminate all bacteria which is an advantage since a small number of microorganisms stimulate wound healing. The invention replaces the use of topical antibiotics, and hence reduces the spread of antibiotic resistant organisms.

Since the products of the invention have an integrated moisture-holding matrix such as a gel or foam, the products of the invention are ideal for treatment of drier wounds. The products protect the wound, absorb exudate and reduce the number of pathogenic microorganisms, without using antimicrobial substances and adds moisture to the wound both supporting the hydrophobic functioning of the pad and healing in general by keeping the wound moist.

An alternative method to lift the microbes from the wound and still keep the wound moist is the electrostatic solution (such as described in U.S. Patent application 2006/0163149) used in layer 14 together with foam or gel. A further method to lift the microbes and still keep the moist, is to use the hydrophobic method in combination with the electrostatic method together with gel or foam.

Other objects and features of the inventions will be more fully apparent from the following examples and appended claims.

Example 1

Manufacture of Wound Dressing Product with Gel as the Moisturizing Matrix

In this example we manufacture a gel based wound dressing based on the invention in the following manner:

Materials: (from Inside-Out See FIG. 1a)

| LAYER | COMMERCIAL PRODUCT NAME | SUPPLIER |
| --- | --- | --- |
| 1. Moisturizing gel | Syntalen K | Vendiko Chemical AB Malmö |
| 2. Hydrophobic layer | Green Cellulose Acetate woven prepared according to U.S. Pat. No. 4,617,326 | ABIGO Medical AB Sweden |

The hydrophobic layer is preferably produced according to U.S. Pat. No. 4,617,326 by applying to a cellulose acetate fabric an amount of dioctadecyl carbamoyl chloride as disclosed in this patent making a covalent bond between the materials. The acetate fabric is on rolls at a width of 1 m, and taken as such to the next step.

A packaging-film which also serves as a carrier-film during the production is used. This film is preferably made of an aluminum foil, and most preferably of foil having a plastic layer on both sides, such as a Polyethylene terephthalate laminated aluminum foil and with a polyethylene surface on the inside for welding the packaging, for example, PET70/ALU6,35/PE70 (by Stenqvist AB, SE-260 50 Billesholm, Sweden). One further option is to have foil of peel-open type, as known in the industry, for easier use by the final user.

1. The foil is placed in an assembling machine where the lower foil of the package is fed on a continuous line over a surface for the assembly.
2. On the foil is firstly the gel placed by pumping and distributing the gel evenly over an area of 75×150 mm on the foil. The amount of gel used is preferably 11-17 gram for this size of the product, but can be varied between 3-30 grams.
3. The hydrophobic layer of acetate fabric is cut into suitable size pieces for the final product, which in this example is 75×150 mm. The cut pieces are placed on top of the gel area on the foil.
4. Over the now assembled product with a bottom packaging foil, layer of gel and the acetate fabric, is now a top foil placed of the same type as the bottom foil. The package foil is then welded to create the finished and packaged product.

The now completely assembled dressing, is finally sterilized (Isotron Gamma Irradiation, Netherlands) and then packed.

Example 2

Manufacture of Wound Dressing Product with Foam as the Moisturizing Matrix

In this example we manufacture a foam based wound dressing based on the invention in the following manner:
Materials: (from Inside-Out See FIG. 2a)

| LAYER | COMMERCIAL PRODUCT NAME | MANUFACTURER |
|---|---|---|
| 1. Hydrophobic layer | Green Cellulose Acetate woven prepared according to U.S. Pat. No. 4,617,326 | ABIGO Medical AB Sweden |
| 2. Adhesive | Disponal 70 | Limgrossisten AB, Norrköping, Sweden |
| 3. Moisturizing foam | Bulpren S 31062, about 75 ppi (pore per inch) | ABC Eurosoft AB, Bjuv, Sweden |

The hydrophobic layer is preferably produced according to U.S. Pat. No. 4,617,326 by applying to a cellulose acetate fabric an amount of dioctadecyl carbamoyl chloride as disclosed in this patent making a covalent bond between the materials. The acetate fabric is on rolls at a width of 1 m, and taken as such to the next step.

The adhesive component, Disponal 70 (Limgrossisten AB, Norrkoping, Sweden), is applied to the foam material by using a slot applier, spraying or roll coating, such as reverse roll, direct roll, 5-roll multi-roll, 3-roll offset, offset gravure, die, pressure, saturators, rod, and Meyer rod coating as a very thin layer at an amount of <10 g/m$^2$, preferably <8 g/m$^2$ and then laminated with the foam layer, (Bulpren S 31062), between two rollers for the final bonding.

The now bonded hydrophobic layer and foam layer is cut into suitable size pieces for the final product, in this case 30 mm×30 mm. The completely assembled dressing, is finally sterilized (Isotron Gamma Irradiation, Netherlands) and then packed in cartons.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A dressing for a wound consisting essentially of:
a first layer, wherein the first layer is a hydrophobic layer that binds microorganisms when the dressing is placed on the wound, and wherein the first layer has been treated with a compound that contains hydrophobic groups and the compound is selected from the group consisting of a dialkyl carbamoyl chloride and an alkyl ketene dimer; and
a second layer comprising a foam that is attached to the first layer,
wherein, when the dressing is applied to the wound, the first layer is between the second layer and the wound, and a surface of the first layer is configured to be in direct contact with the wound,
wherein moisture is trapped by the foam and supports hydrophobic functioning of the dressing that helps bind microorganisms to the first layer without the use of antimicrobial compounds, and
wherein the foam consists of a polyether foam, polyester foam, or polyurethane foam.

2. The dressing of claim 1, wherein the foam is a polyether foam.

3. The dressing of claim 1, wherein the hydrophobic layer is bonded to the foam.

4. The dressing of claim 1, wherein the hydrophobic layer is bonded to the foam with an adhesive.

5. The dressing of claim 1, wherein the hydrophobic layer comprises a woven or non-woven fabric.

6. The dressing of claim 1, wherein the hydrophobic layer comprises a hydrophilic fabric.

7. The dressing of claim 1, wherein the hydrophobic layer is made of cellulose acetate and the compound is dioctadecyl carbamoyl chloride, and wherein the dioctadecyl carbamoyl chloride is applied to the cellulose acetate.

8. The dressing of claim 1, wherein the compound is a dialkyl carbamoyl chloride selected from the group consisting of dihexadecyl-carbamoyl chloride and dioctadecyl-carbamoyl chloride.

9. The dressing of claim 1, wherein the foam is a polyurethane foam.

10. A dressing for a wound consisting essentially of:
a hydrophobic layer that binds microorganisms when the dressing is placed on the wound, wherein the hydrophobic layer has been treated with a compound selected from the group consisting of a dialkyl carbamoyl chloride and an alkyl ketene dimer; and
a foam layer attached to the hydrophobic layer, wherein, when the dressing is placed on the wound, a surface of the hydrophobic layer is configured to be in direct contact with a surface of the wound, and
wherein moisture is trapped by the foam layer and supports hydrophobic functioning of the dressing that helps bind microorganisms to the hydrophobic layer without the use of antimicrobial compounds.

11. The dressing of claim 10, wherein the foam layer is selected from the group consisting of polyether, polyester, and cellulose.

12. The dressing of claim 10, wherein the foam layer comprises a polyurethane foam.

13. The dressing of claim 10, wherein the hydrophobic layer is bonded to the foam layer with an adhesive.

14. The dressing of claim 10, wherein the hydrophobic layer comprises a woven or non-woven fabric.

15. The dressing of claim 10, wherein the hydrophobic layer is made of cellulose acetate and the compound is dioctadecyl carbamoyl chloride, and wherein the dioctadecyl carbamoyl chloride is applied to the cellulose acetate.

16. The dressing of claim 10, wherein the compound is a dialkyl carbamoyl chloride selected from the group consisting of dihexadecyl-carbamoyl chloride and dioctadecyl-carbamoyl chloride.

17. The dressing of claim 10, wherein the foam consists of a polyether foam, polyester foam, or polyurethane foam.

18. A dressing for a wound consisting essentially of:
    a fabric layer, wherein the fabric layer comprises at least one hydrophobic fabric that binds microorganisms, wherein the at least one hydrophobic fabric is a fabric comprising a compound that contains hydrophobic groups, and wherein the compound is selected from the group consisting of a dialkyl carbamoyl chloride and an alkyl ketene dimer; and
    a foam layer that is attached to the fabric layer,
    wherein, when the dressing is applied to the wound, a surface of the fabric layer is configured to be in direct contact with a surface of the wound.

19. The dressing of claim 18, wherein the at least one hydrophobic fabric is a cellulose acetate fabric treated with a compound that contains hydrophobic groups.

20. The dressing of claim 18, wherein the foam layer comprises a polyurethane foam.

21. The dressing of claim 18, wherein the foam layer is selected from the group consisting of polyether, polyester, and cellulose.

22. The dressing of claim 18, wherein the foam layer traps moisture and aids in the binding of microorganisms to the at least one hydrophobic fabric.

23. The dressing of claim 18, wherein the dressing does not include an antimicrobial compound.

24. The dressing of claim 18, wherein the fabric layer is bonded to the foam layer with an adhesive.

25. The dressing of claim 18, wherein the foam consists of a polyether foam, polyester foam, or polyurethane foam.

* * * * *

UNITED STATES PATENT AND TRADEMARK OFFICE
CERTIFICATE OF CORRECTION

PATENT NO. : 10,893,981 B2
APPLICATION NO. : 15/256841
DATED : January 19, 2021
INVENTOR(S) : Robertsson et al.

Page 1 of 1

It is certified that error appears in the above-identified patent and that said Letters Patent is hereby corrected as shown below:

On the Title Page (56) References Cited, U.S. PATENT DOCUMENTS, Page 2, Column 1, Bogart et al. cite:
Please correct "5,271,043" to read -- 5,271,943 --

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*